United States Patent [19]
Hansen

[11] Patent Number: 6,162,965
[45] Date of Patent: Dec. 19, 2000

[54] PLANT TRANSFORMATION METHODS

[75] Inventor: Geneviève Hansen, Durham, N.C.

[73] Assignee: Novartis AG, Basel, Switzerland

[21] Appl. No.: 09/089,111

[22] Filed: Jun. 2, 1998

Related U.S. Application Data

[60] Provisional application No. 60/098,564, Jun. 2, 1997.

[51] Int. Cl.$^7$ ............................ C12N 15/82; C12N 15/84; C12N 5/04; A01H 4/00; A01H 5/00
[52] U.S. Cl. ........................ 800/278; 800/298; 800/320; 800/320.1; 800/278; 800/283; 435/172.3; 435/252.2; 435/320.1; 435/410; 435/411; 435/419
[58] Field of Search .................................... 800/298, 283, 800/278, 279, 285, 320.1, 320; 435/172.3, 252.2, 320.1, 410, 411, 419

[56] References Cited

U.S. PATENT DOCUMENTS 5,464,763   11/1995   Schilperoort et al. .................. 800/294
5,591,616    1/1997   Hiei et al. ............................ 435/172.3

FOREIGN PATENT DOCUMENTS

WO/99/47688   9/1999   WIPO .

OTHER PUBLICATIONS

Clem et al., "Control of Programmed Cell Death by the Baculovirus Genes p35 and iap," *Molecular and Cellular Biology*, 14(8): 5212–5222 (1994).
Deng et al., "T–DNA Genes Responsible for inducing a Necrotic Response on Grape Vines," *Molecular Plant–Microbe Interactions*, 8(4): 538–548 (1995).
Enriquez–Obregón et al., "Genetic Transformation of Sugarcane by *Agrobacterium tumefaciens* Using Antioxidant Compounds," *Biotecnologia Aplicada*, 14(3): 169–174 (1997).
Ishida et al., "High efficiency transformation of maize (*Zea mays* L.) mediated by *Agrobacterium tumefaciens*," *Nature Biotechnology*, 14: 745–750 (1996).
Perl et al., "Establishment of an Agrobacterium–mediated transformation system for grape (*Vitis vinifera* L.): The role of antioxidants during grape–Agrobacterium interactions," *Nature Biotechnology*, 14: 624–628 (1996).
Pu et al., "Induction of Necrogenesis by *Agrobacterium tumefaciens* on Grape Stem Explants," *Molecular Plant–Microbe Interactions*, 8: Abstract (A40) (1995).
Tanaka et al., "dad–1, A Putative Programmed Cell Death Suppressor Gene in Rice," *Plant Cell Physiology*, 38(3): 379–383 (1997).
PCT/EP 98/03215 International Search Report (Dec. 1998).
Millra et al. Plant Cell. vol. 10, 1889–1902, 1998.
Toriyama et al. Theor. Appl. Genet. 1991. vol. 81: 769–776.
Boase et al. In Vitro Cellular and Developmental Biology, 1998. vol. 34: 46–51.
Raineri, D.M. et al., Bio/Technology, 8: pp. 33–38 (1990).
Barrett et al. Plant Cell Tissue Organ Culture. 1997. vol. 47: 135–144.
Napoli et al. The Plant Cell. 1989. vol. 2: 278–289.
Enriquez–Obregon et al. Biotecnologia Aplica. 1997. vol. 14: 169–174.
Ishida et al. Nature Biotechnology. 1996. vol. 14: 745–750.
Hiei et al. The Plant J. 1994. vol. 6: 271–282.
De Block et al. Plant Physiol. 1989. vol. 91: 694–701.
Gordon–Kamm et al. The Plant Cell. 1990. vol. 2: 603–618.
Potrykus, I., 1990, Bio/Technology, 6(6):535–542.
Wu et al., 1995, The Plant Cell, 7:1357–1368.
Levine et al., Cell, 1994, 79:583–593.
Boulton et al., *Plant Molecular Biology*, 12:31–40, 1989.
Orzaez et al., *The Plant Journal*, 11(1):137–144, 1997.
Perl, et al., *Plant Cell Reports*, 7:403–406, 1988.
Songstad et al., *Plant Cell Reports*, 7:262–265, 1988.
Wang et al., *Plant Molecular Biology*, 32:1125–1134, 1996.

*Primary Examiner*—Lynette R. F. Smith
*Assistant Examiner*—Ousama Zaghmout
*Attorney, Agent, or Firm*—George Jen; Edouard G. Lebel; Thomas Hoxie

[57] ABSTRACT

An improved method of Agrobacterium transformation of plants, particularly Gramineae, is provided, utilizing conditions capable of inhibiting Agrobacterium-induced necrosis.

48 Claims, No Drawings

PLANT TRANSFORMATION METHODS

This application claims the benefit of U.S. provisional application Ser. No. 60/098,564, filed Jun. 2, 1997.

This invention relates to a method of transforming plants using Agrobacterium by carrying out the transformation in the presence of an agent which inhibits Agrobacterium-induced necrosis and/or using a strain of Agrobacterium which does not induce necrosis.

The first method and still one of the most widely used methods for the introduction of foreign genetic material into plants exploits the natural transformation system of Agrobacterium spp. using recombinant Ti (tumor-inducing) or Ri (root-inducing) plasmids wherein the T-DNA comprises a gene of interest. The gene of interest is incorporated into the plant's genetic material by the same mechanism as is used in the natural system to incorporate the oncogenes or opine biosynthesis genes.

While Agrobacterium transformation works well for plants which are naturally infected and transformed by Agrobacterium in the wild to form tumors and/or hairy roots, it does not work well for other plants. For example, members of the grass family (Gramineae) such as maize, are not known to form tumors upon exposure to Agrobacterium and have generally proved to be extremely recalcitrant to Agrobacterium transformation. Ishida, et al. Nature Biotechnology (1996) 14: 745–750 have reported transformation of embryos from a particular maize line (A188) and its hybrids using Agrobacterium having "super-binary" vectors, but the reproduceability of these results and the applicability of this system to other maize lines and or using Agrobacterium having other vectors is unclear. There have also been reports of Agrobacterium transformation of maize using apical meristem as target tissue, but the low efficiency of apical meristem as a target tissue compared to, e.g., embryogenic callus, make this approach less than optimal. Even some dicotyledonous plants such as grapes, soybeans or pepper which are susceptible to Agrobacterium infection and tumor formation in the wild have nevertheless proved difficult to transform in the laboratory because the preferred target tissues for transformation and regeneration seem to respond poorly to Agrobacterium exposure. The lack of understanding as to the mechanisms of resistance to Agrobacterium infection and tumor formation has proved an obstacle to devising a solution to or even to properly evaluating the problem of Agrobacterium transformation in plants recalcitrant to Agrobacterium transformation, such as Gramineae.

It has now surprisingly been discovered that Agrobacterium is capable of inducing apoptotic necrosis in plant cells, particularly of the family Graminieae, e.g., maize. Methods of selecting and generating Agrobacterium which are less competent to induce necrosis have been discovered, as have methods of inhibiting the necrosis response in cells to be transformed.

The necrosis seen in Gramineae cell culture upon exposure to Agrobacterium is a programmed cell death by which the cell, apparently through a signal transduction mechanism, directs its own death. It is distinct from passive cell death, i.e., necrosis involving disruption of membrane integrity and subsequent swelling that results in lysis, for example as is seen upon exposure to various toxins. Cells undergoing programmed cell death show characteristic morphological changes and DNA fragmentation, which, collectively, define the process of apoptosis and are implemented by a mechanism involving de novo gene expression. The stereotypic characteristics of apoptosis described in animal cells are shrinkage, loss of cell-to-cell contact in organized tissues, condensation of the nucleus and chromatin, fragmentation of DNA (DNA "laddering") and nuclear and membrane blebbing. We have shown that cocultivation of Agrobacterium with maize or wheat tissues results in a process closely analogous to apoptosis in animal cells, wherein cell death is characterized by DNA cleavage into oligonucleosomal fragments and defined morphological changes. In maize cells exposed to Agrobacterium, $Ca^{2+}$ increases the intensity of DNA fragmentation whereas $Zn^{2+}$ has the opposite effect, which parallels the effect of these divalent cations on endogenous endonucleases responsible for DNA cleavage during apoptosis in animal cells. This fragmentation is also decreased by addition of cycloheximide, which is evidence that the process requires de novo gene expression. Programmed cell death in response to exposure to Agrobacterium has not previously been reported.

It has further been discovered that this Agrobacterium-induced necrosis (AIN) observed in Gramineae can be inhibited by the use of AIN-inhibiting agents, either chemical compounds such as silver nitrate, or AIN-inhibiting nucleotide sequences stably integrated or transiently operative in the cell to be transformed. It has also been discovered by screening collections of Agrobacterium that Agrobacterium strains vary in their ability to induce necrosis, so that strains can be selected which are suitable for transforming recalcitrant plants such as Gramineae.

Accordingly, the several embodiments of the invention include the following:

1. A method of transforming a plant cell with a gene of interest, comprising exposing said plant cell to Agrobacterium under conditions which inhibit AIN such as the presence of an AIN-inhibiting agent or heat shock treatment, wherein said Agrobacterium comprises one or more plasmids (vectors) comprising one or more genes of interest.

1.1. In one embodiment of the foregoing method, the AIN-inhibiting agent is a chemical inhibitor. The chemical inhibitor is preferably a compound selected from the group consisting of ethylene inhibitors (e.g., 2,5-norbornadiene, norbornene, silver thiosulfate, and silver nitrate), ethylene synthesis inhibitors (e.g., aminoethoxyvinylglycine (AVG), cobalt salts, acetyl salicylic acid, or salicylic acid), gibberelin antagonists (e.g., abscisic acid (ABA)) and phophatase inhibitors (e.g., okadaic acid). Most preferably, the chemical inhibitor is an ethylene inhibitor, preferably silver nitrate. Proteins and peptides can act as chemical inhibitors as well. Examples are naturally occurring proteins such as DAD-1, the baculovirus inhibitors of apoptosis (IAPs), baculovirus p35, or synthetic peptide analogs of caspases capable of triggering apoptosis. A chemical inhibitor is suitably present in an effective concentration , e.g., for silver nitrate in a concentration of from 0.1 to 20 mg/l, preferably 1 to 10 mg/l.

1.2.1. In an alternative embodiment of this method, the AIN-inhibiting agent is a nucleotide sequence. The AIN-inhibiting nucleotide sequence may inhibit AIN directly or by encoding an AIN-inhibiting mRNA coding for an AIN-inhibiting protein. For example, it may be an antisense oligonucleotide or a gene encoding antisense mRNA, which is antisense to a gene encoding a necrosis associated enzyme (e.g., protease, kinase, or phosphatase) or regulatory protein. Alternatively, it may comprise the coding region of a gene capable of inhibiting apoptosis under control of a promoter capable of expression in plants, e.g., a coding region of a mammalian bcl-1 gene under control of a promoter capable of expression in plants, a coding region of an apoptosis-inhibiting gene from a baculovirus such as p35 or pIAP, or a gene capable of suppressing disease response in plants, e.g., nahG, dad-1, or mlo. An AIN-inhibiting nucleotide sequence expressing an AIN-inhibiting protein may optionally be adapted for expression in the host plant by making a synthetic nucleotide sequence encoding the same protein but using codons which are preferred by the host plant and avoiding nucleotide sequences, e.g., polyadenylation signals or splice sites within the coding region, which may affect optimal expression in the host plant, e.g., analogously to the methods described in U.S. Pat. No. 5,380,831 or U.S. Pat. No. 5,610,042.

1.2.2. The AIN-inhibiting nucleotide sequence may be stably incorporated into the genome of the plant to be transformed or may be only transiently present and operable, e.g., at or around the time the cell is exposed to the Agrobacterium. Transient expression can be obtained, e.g., using an agroinfection system, wherein the T-DNA carries two gemini viruses in tandem such that a viral replicon that carries the AIN-inhibiting nucleotide sequence may replicate in the cell. In this system, the virus typically will not integrate into the plant genome but will replicate to a high copy number and provide a high level of transient expression. Cells thus primed to be resistant to necrosis can then be transformed using Agrobacterium having Ti plasmids comprising the gene of interest, which will be incorporated into the genome, while the virus is diluted through regeneration and will not be transmitted to the seed. Thus the progeny and descendants of the infected plant are stably transformed with the gene of interest but not with the AIN-inhibiting nucleotide sequence. Transient expression may alternatively be obtained by introducing short AIN-inhibiting oligonucleotide sequences into the plant, e.g., antisense sequences.

1.3. In a further alternative embodiment AIN is reduced or inhibited by heat-shock treatment of the plant tissue to be transformed prior to cocultivation with Agrobacterium. The heat shock treatment is performed at 40–50° C., preferably at 42–48° C., 45° C. being a preferred temperature for maize. The treatment lasts for 2–10 minutes and preferably 4–8 minutes.

2. A method of making a fertile, transgenic plant comprising transforming plant tissue by the method of 1 above, and regenerating the tissue thus transformed. Preferably, the tissue is selected from immature embryos or embryogenic calli, e.g., maize type I callus. Where the tissue is immature embryo, the method preferably further comprises placing the embryos on callus initiation medium either before or after exposure to Agrobacterium and regenerating the plant from the embryogenic callus thus obtained. Preferably, the gene of interest (or one of them) is a selectable or scorable marker, permitting selection or identification of transformed cells, transformed tissue and/or regenerated transformed plants.

3. The use of an AIN-inhibiting agent, e.g., a chemical inhibitor of AIN (for example an ethylene inhibitor, e.g., silver nitrate) or an AIN-inhibiting nucleotide sequence (for example one encoding for an AIN-inhibiting mRNA or protein) in a method of Agrobacterium transformation of a plant or tissue or cell thereof or a method of making a fertile transgenic plant, e.g., a method according to 1 or 2 above.

4. A transgenic plant produced by the method of 2 above, or seed or progeny thereof 5. A plant, plant tissue or plant cell comprising a nucleotide sequence of heterologous origin which inhibits AIN, e.g., a synthetic nucleotide sequence or a nucleotide sequence derived from the genome of a different species of organism.

6. A culture of plant cells or tissues, e.g., for use in transformation of Gramineae, comprising
  a) a chemical inhibitor of AIN,
  b) an Agrobacterium comprising a plasmid comprising a gene of interest, and
  c) water and essential salts.

The chemical inhibitor is suitably present in a necrosis-inhibiting concentration. The chemical inhibitor is preferably a compound selected from the group consisting of ethylene inhibitors (e.g., 2,5-norbornadiene, norbornene, silver thiosulfate, and silver nitrate), ethylene synthesis inhibitors (e.g., aminoethoxyvinylglycine (AVG), cobalt salts, acetyl salicylic acid, or salicylic acid), gibberelin antagonists (e.g., abscisic acid (ABA)) and phophatase inhibitors (e.g., okadaic acid). Most preferably, the chemical inhibitor is silver nitrate, e.g., in a concentration of from 0.1 to 20 mg/l, preferably 1 to 10 mg/l. The optimal composition and concentration of essential salts are as known in the art and may vary somewhat depending on the species, type, and stage of development of the cells or tissue, but are generally such that the ion and nutrient concentrations of the medium (e.g. concentrations of nitrates, potassium ions, phosphates, calcium ions, magnesium ions, sodium ions, and chlorine ions) are maintained at levels which are well tolerated by the plant cells and by the Agrobacterium. The culture medium may optionally further comprise suitable nutrients (e.g., sugars, for example sucrose), vitamins, amino acids, hormones and other components (e.g., 2, 4-D) as known in the art of plant cell or tissue culture. The plant is preferably of the family Gramineae, e.g., maize. The cells or tissues preferably comprise embryogenic callus, e.g., Type I or Type II callus.

7. A method of transforming a totipotent cell of a plant of the family Gramineae, comprising exposing a population of totipotent cells or tissue comprising totipotent cells to Agrobacterium comprising one or more plasmids comprising one or more genes of interest, wherein the Agrobacterium is of a strain which does not induce significant levels of necrosis in said population at an exposure duration and concentration sufficient to achieve transformation of said cell. The tissue is preferably other than apical meristem, e.g., preferably undifferentiated tissue, e.g., plated zygotic embryos or embryogenic callus, preferably embryogenic callus during initiation phase (e.g., up to 28 days, preferably up to 14 days from plating on initiation medium), or serially propagatable embryogenic callus, e.g., Type I or Type II callus.

8. A method for determining the suitability of an Agrobacterium strain for use in the transformation of a regenerable cell of a plant of the family Gramineae comprising exposing a population of said regenerable cells of the plant to the Agrobacterium strain and observing or determining the amount of necrosis in said cell population.

9. An Agrobacterium strain which has been genetically modified to reduce or eliminate expression of the Agrobacterium necrosis factor or a derivative of such a modified strain. Agrobacterium necrosis factor is the heat labile factor observed in concentrated supernatant capable of inducing necrosis, e.g., programmed cell death, in maize embryos. The incompatibility between Agrobacterium and maize cells likely involves some genetic components. The present invention describes three genes from Agrobacterium involved in the cell death response of maize tissues. They are identified by screening a BAC library of Agrobacterium. 3 independent BAC are found to elicit cell death and show homology with xylA-xylB, virB1 and acvB. It is possible that the genes reported are only a subset of the genes responsible for the incompatibility of Agrobacterium with maize tissues. The plant cell used in the methods of the invention is preferably from a plant species or variety which does not produce galls or hairy roots upon Agrobacterium transformation. Preferably the plant species is a member of the grass family (Gramineae), most preferably maize or wheat, especially maize. The plant cell is preferably a totipotent cell, i.e., a cell which is capable of regenerating itself into a plant, preferably a fertile plant. Totipotent cells are present, e.g., in immature embryos and embryogenic calli. The target tissue is preferably other than apical meristem. More preferably, the target tissue comprises undifferentiated tissue, e.g., plated zygotic embryos or embryogenic callus. The embryogenic callus may be associated with the embryo during the callus initiation phase (e.g., the period up to 28 days, preferably up to 14 days from plating of the immature embryo on initiation medium), or may be serially propagatable embryogenic callus, e.g., Type I or Type II callus. Maize Type I callus is a preferred tissue comprising totipotent cells for use in the present invention.

The Agrobacterium is preferably selected from A. tumefaciens and A. rhizogenes. Preferably the Agrobacterium strain is an A. tumefaciens strain, most preferably a nopaline-utilizing strain. When the Agrobacterium strain is an A. rhizogenes strain, it is preferably an agropine- or mannopine-utilizing strain. Most preferably, the Agrobacterium is an Agrobacterium which does not induce necrosis in Gramineae, e.g., an Agrobacterium selected from A. tumefaciens strains A and B. Agrobacterium strains A and B have been deposited with the American Type Culture Collection (ATCC) 12301 Parklawn Drive, Rockville, Md. 20852/ USA, under ATCC Designation numbers 55964 and 55965 respectively on May 2, 1997, pursuant to the Budapest Treaty.

The gene of interest is preferably a gene for herbicide resistance, disease resistance, or insect resistance, or is a selectable or scorable marker, and comprises a plant-operable promoter, a coding region, and a 3' terminator region. Herbicide resistance genes include the AHAS gene for resistance to imidazolinone or sulfonyl urea herbicides, the pat or bar gene for resistance to bialaphos or glufosinate, the EPSP synthase gene for resistance to glyphosate, etc. Disease resistance genes include genes for antibiotic synthetic enzymes, e.g., for pyrolnitrin synthetic enzymes, plant derived resistance genes, and the like. Insect resistance genes include genes for insecticidal proteins from *Bacillus thuringiensis*. Selectable markers include herbicide resistance genes and antibiotic (e.g., hygromycin or kanamycin) resistance genes, as well as positive selectable markers, such as the gene for mannose phosphate isomerase. Scorable markers include genes for readily assayable enzymes such as the gus gene and the cat gene. The plasmid may comprise more than one gene of interest and/or the Agrobacterium may comprise different plasmids having different genes of interest.

The term Agrobacterium-induced necrosis (AIN) as used herein refers to any Agrobacterium-mediated plant cell death, but particularly includes Agrobacterium induced programmed cell death.

EXAMPLES

Example 1

Mechanism of Action of Necrosis in Maize Exposed to Agrobacterium a. Demonstration of necrosis of maize but not tobacco in presence of Agrobacterium Maize embryogenic calli and embryos have proven to be particularly difficult tissues for transformation by Agrobacterium. The following experiments employ maize inbred lines (*Zea mays L.*) HE/89 and a line here designated as Elite 1. Friable embryogenic callus of the maize line HE/89 was provided by Gunter Donn. HE/89 is described in Morocz, S., Donn, G., Németh, J. and Dudits, D. (1990) *Theor. Appl. Genet.* 80:721–726). Elite 1 is a Novartis proprietary elite line related to B73. Suspension culture of Elite 1 is initiated from friable embryogenic callus selected from immature embryos. The HE/89 line is grown in a modified liquid N6 medium amended with 500 mg/l Bacto tryptone, 30 g/l sucrose and 0.5 mg/l 2,4-dichlorophenoxy acetic acid (2,4-D) (N6M). The Elite 1 line is grown in N6 liquid medium (Chu et al., 1975) supplemented with 30 g/l sucrose and 2 mg/l 2,4-D (2N63S). The *Nicotiana tabacum* cell line NT-1 grown in Murashige and Skoog medium supplemented with 2 mg/l of 2,4-D and sucrose (30 g/l) (MS3S) is used as an Agrobacterium-susceptible control. Suspension cultures are maintained in liquid medium on a rotary shaker (120 rpm) and are subcultured every 7 days.

Bacteria are grown in YP medium (5 g/L yeast extract, 10 g/l peptone, 5 g/l NaCl, pH 6.8) for 24 hr at 28° C. Bacteria are centrifuged and resuspended in the appropriate plant medium. For the inoculation of Elite 1, HE/89 and NT-1 plant cells, bacteria are resuspended in 2N63SM, N6M and MS3S liquid medium respectively.

Soon after inoculation of maize embryogenic callus, many of the cells turn necrotic (Table 1). Necrosis is observed even after the transfer of the treated embryogenic calli to a bacteriae free-, cefotaxime-containing medium. Cocultivation of maize cells with very diluted cultures of Agrobacterium for a very short time is sufficient to induce necrotic response or inhibition of growth of the maize inbred Elite 1. For HE/89 embryogenic calli, a short time of cocultivation reduces necrotic change to some extent, but does not completely prevent necrosis. In control experiments, cefotaxime does not cause the maize tissue to become necrotic. Thus, it appears that the necrotic effect is a consequence of the interaction between Agrobacterium and maize calli. As control, NT1 tobacco cells are also inoculated with Agrobacterium and no necrogenesis is observed.

TABLE 1

Cocultivation of plant suspension cells with LBA4404

|  | HE/89 | | | Elite | | |
| --- | --- | --- | --- | --- | --- | --- |
|  | 2 days | 4 days | 7 days | 2 days | 4 days | 7 days |
| No Agrobacterium OD = 0.2 | – | – | – | – | – | – |
| 10 min | – | – | + | – | + | + |
| 1 hr | – | – | + | + | + | ++ |
| 24 hrs | – | + | + | + | + | ++ |
| 48 hrs | + | + | ++ | + | ++ | +++ |
| OD = 1 |  |  |  |  |  |  |
| 10 min | – | + | + | + | + | + |
| 1 hr | – | + | + | + | + | ++ |
| 24 hrs | + | + | ++ | + | ++ | ++++ |
| 48 hrs | + | + | ++ | ++ | +++ | ++++ |

Friable embryogenic callus of HE/89 maize and of a proprietary elite inbred maize maintained in liquid medium are incubated with Agrobacterium for 10 min, 1 hr, 24 hr or 48 hrs prior to transfer to cefotaxim-containing medium. 50 μl of bacteria at an optical density indicated (OD = 600 nm) is added to 10 ml of tissue culture medium containing 1 ml of packed cell volume. If the culture is to be incubated longer than two days, bacteria are washed off and plant cells are resuspended in the same medium supplemented with cefotaxime (250 mg/l). The presence or absence of necrosis is scored 2, 4 and 7 days after inoculation and the relative intensity of necrosis is expressed as follow: +, rare formation of necrosis; ++, weak necrosis; +++, strong necrosis; ++++, very strong necrosis.

b. Evidence for Programmed Cell Death

In order to determine the mechanism of cell death induced by Agrobacterium in maize tissues, genomic DNA is extracted from plant suspension cells harvested 24 or 48 hours after inoculation with Agrobacterium. Exposure to Agrobacterium causes DNA fragmentation in both maize lines, with a pattern characteristic of internucleosomal fragmentation, which is considered an early hallmark of programmed cell death. Control maize cells and tobacco cells, maintained in culture medium alone, do not show DNA fragmentation under these conditions. Inoculation of maize cells with *E. coli* or with autoclaved Agrobacterium cells does not cause DNA fragmentation. Furthermore, maize cells undergoing programmed cell death could not induce cell death of fresh maize embryogenic tissues.

Further evidence for Agrobacterium inducing DNA fragmentation is obtained by investigating the sensitivity of the process to $Zn^{2+}$ and $Ca^{2+}$. In the cell line HE/89, $Ca^{2+}$ increased the intensity of DNA ladders whereas $Zn^{2+}$ markedly reduced genomic fragmentation. These characteristics are fully consistent with the effect of these divalent cations on the endogenous endonucleases responsible for DNA cleavage during apoptosis in animal system. The intensity of the ladder also is decreased by addition of cycloheximide, evidence that the process requires de novo gene expression. These results indicate that the contact of Agrobacterium with maize cells accounts for the cell death of maize tissues. Fragmentation of DNA during apoptosis is also detected in situ by reagents that react with the exposed hydroxyls on the nucleosome units. 12 day old maize embryos from a proprietary elite line of Lancaster parentage are inoculated with LBA4404 and plated on DG4 medium supplemented with chloramben. Koziel, M. G., & al. 1993. *Bio/Technology* 11: 194–200. Apoptotic cells are detected by in situ staining with TACS-1 kit (Trevigen), which involves end labeling the DNA fragments by the klenow enzyme using dNTP conjugated to a detectable marker, giving a dark insoluble precipitate indicative of genomic fragmentation. Cullivier, O., Pirianov, G., Kleuser, B., Vanek, P. G., Coso, O. A., Gutking, J. S. and Spiegel, S. (1996) *Nature* 381, 800–803. Embryos are soaked in 3.7% formadehyde solution and processed as described by the manufacturer. To detect genomic DNA cleavage in situ, fixed embryos are treated with the TACS-1 kit. Fixed cross-sections are first treated with proteinase K for 5 min at room temperature and then dipped for 5 min into 2% hydrogen peroxide to remove endogenous peroxidase. After a brief wash with klenow buffer, tissues were then incubated for 1 hr at 37° C. with the klenow enzyme that can incorporate exogenous modified deoxynucleotides to the 5' termini of the cleaved fragments. A dark insoluble precipitate indicative of apoptosis that appears in the individual cell is detectable with a microscope.

Agrobacterium-treated cells become darkened and distorted in shape after 48-hr exposure. Control embryos, maintained in culture medium alone or inoculated with *E.coli*, do not show any precipitate under these conditions. It is also found that not all maize tissues react similarly to an Agrobacterium infection: shoots remain intact whereas embryos turn necrotic. DNA fragmentation is also observed with Agrobacterium strains cured of the pathogenic plasmid (Strains A136 and LBA4402), suggesting that the factor inducing programmed cell death is unrelated to the plasmid. Programmed cell death is also observed when maize embryos are incubated for 20 minutes with supernatant concentrated 20-fold from a cell death inducing Agrobacterium (strain LBA 4404), but not when embryos are contacted with supernatant prepared in the same way from *E. coli*. Programmed cell death also does not occur if the concentrated Agrobacterium supernatant is heated for 20 minutes at 100° C. prior to incubation.

Maize embryogenic calli often contain areas of cells still apparently alive and other areas which are necrotic. The fact that only limited areas die, even in situations in which cells outside the responding area are exposed simultaneously to the stimulus suggests that temporal or permanent diversity exists in elements controlling the response of individual cells to different stimuli in organized tissues. The number of cells in an organized tissue undergoing programmed cell death may be small compared with the total mass and the process may be asynchronous. The induction of PCD in one or a few cells in a given area or tissue may trigger the rapid death of surrounding cells as observed in animal cells, and the latter cells may not show the programmed cell death phenotype but die nonetheless.

Example 2

Inhibition of Agrobacterium-induced Programmed Cell Death

Preparation of Tissues for Inoculation with Agrobacterium:

Immature embryos (1.2 to 2.2 mm in length) are aseptically excised 14–15 days after pollination from surface-sterilized, greenhouse-grown ears and plated scutellum up on callus initiation medium, 2DG4+5 mg/l chloramben (2DG4-5 Chl). 2DG4 medium is Duncan's medium modified to contain 20 mg/l sucrose.

Embryos with Callus Response:

Immature embryos are sterilized as described above and plated on callus initiation medium (2DG4-5 Chl) and cultured therein for 1 to 7 days. The resulting tissue is used as samples for inoculation.

Young Type I Callus:

Embryos plated on callus initiation medium (2DG4+5 Chloramben) for 7 to 20 days give rise to callus. These calli are typical type I calli for the maize inbred used, which are compact and relatively well organized clusters of cells. Resultant embryogenic callus are cut out of embryos and transferred to callus maintenance medium, 2DG4+0.5 mg/l (2,4-dichlorophenoxy) acetic acid (2,4-D) and used as samples for inoculation.

Type I Callus:

Type I callus obtained by the method described above can be maintained on the maintenance medium (2DG4+2,4 D 0.5 mg/l) and subcultured every 2 weeks.

Agrobacterium:

Strain A. tumefaciens LBA4404 (pAL4404, pSB1) is used in these experiments. pAL4404 is a disarmed helper plasmid. pSB1 is a wide host range plasmid that contains a region of homology to pGIGUP and a 15.2 kb Kpnl fragment from the virulence region of pTiBo542 (Ishida et al., 1996; High efficiency transformation of maize (*Zea mays L.*) mediated by Agrobacterium tumefaciens, Nature Biotechnology 14, 745–750). The introduction of the plasmid pGIGUP by electroporation into LBA4404(pAL4404, pSB1) results in a cointegration of pGIGUP and pSB1. The T-DNA of this plasmid contains a plant expressible PAT gene driven by the ubiquitin promoter to provide resistance to phosphinothricin and a gene for GUS with an intron in the N-terminal codon of the coding sequence driven by the Gelvin promoter. This intron-GUS gene expresses GUS activity in the plant cell but not in Agrobacterium.

Bacterial Growth:

Agrobacterium is grown for 3 days on YP medium (5 g/l yeast extract, 10 g/l peptone, 5 g/l NaCl, 15 g/l agar, pH 6.8) supplemented with 50 mg/l spectinomycin and 10 mg/l tetracycline. Bacteria are collected with a loop and suspended in N6 liquid medium at a density ranging from $10^9$ to $5 \cdot 10^9$ cells/ml. Agrobacterium cells can also be collected from an overnight culture in YP medium and resuspended in N6 liquid medium.

Co-cultivation in the Presence or Absence of Silver Nitrate:

Maize tissues prepared as described above are inoculated with Agrobacterium. Maize tissues are soaked in the bacterial suspension for 5–10 min and then plated on medium with or without silver nitrate (1 to 10 mg/l). Tissues are also inoculated with a 5 μl drop $10^9$ to $5\times10^9$ cells/ml of an Agrobacterium suspension placed on the top of the tissue. After inoculation, maize tissues are cultured in the dark at 25° C. with or without silver nitrate in the medium (1 to 10 mg/l). 2 or 3 days after inoculation, tissues are transferred on the same medium supplemented with cefotaxime (250 mg/l) with or without silver nitrate.

Results:

Sensitivity of maize embryos and maize embryogenic calli to Agrobacterium. Embryogenic calli can develop from maize embryos of when plated on callus initiation medium. The cell line developed from embryos remains highly embryogenic when maintained on 2,4-D containing medium. The sensitivity of this embryogenic calli and embryos from a maize inbred line to Agrobacterium LBA4404 is assessed. A marked browning of the tissue is observed following cocultivation of Agrobacterium and maize tissues. This reaction is also observed with LBA4402 that is cured of its pathogenic plasmid. Control embryos and embryogenic calli that are cocultivated with *Escherichia coli* and subjected to the same procedures do not exhibit cell death or significant browning. Thus, it appears that the cell death is a consequence of the interaction between maize cells and Agrobacterium. It appears that embryos are more sensitive to Agrobacterium than embryogenic callus. A concentration of $10^9$ cells/ml is enough to induce cell death. Furthermore, a short exposure (5 min) is sufficient to induce this reaction.

The effect of adding silver nitrate to the co-cultivation medium and to the callus initiation medium is determined. Addition of silver nitrate allows recovery of healthy tissues (Tables 2 and 3). About 50% of the embryos plated on medium containing silver nitrate are able to produce embryogenic calli. The optimal effect is obtained with embryos plated on callus initiation medium for at least 2 days prior inoculation with Agrobacterium. The combination of these two factors is found to drastically prevent necrosis of maize embryogenic calli following Agrobacterium co-cultivation.

The reduced browning of the embryogenic calli correlates with callus initiation and survival of the tissue after Agrobacterium inoculation. About 80% of control embryos not treated with Agrobacterium give rise to embryogenic calli.

The effect of silver nitrate is also observed with type I calli inoculated with Agrobacterium (Table 3). It appears that a young line is more resistant to Agrobacterium inoculation and a pretreatment with silver nitrate improves the recovery of healthy tissues.

In order to verify that the presence of the silver nitrate during co-cultivation does not reduce Agrobacterium virulence, tobacco leaf discs are inoculated with LBA4404 (GIGUP) at a concentration of $10^9$ cells/ml. No significant decrease in GUS activity is observed in tobacco leaves.

TABLE 2

Inoculation of maize embryos with LBA4404
Embryos and embryos with embryogenic callus responses are inoculated with Agrobacterium LBA4404 (GIGUP) ($10^9$ cells/ml). The basic medium is 2DG4 + 5Chloramben (2DG4). All treatments are done on about 80 to 100 embryos and repeated twice. Callus initiation is scored two weeks after inoculation.

| Pretreatment (time) | Co-inoculation medium | Transfer | Score |
|---|---|---|---|
| no pretreatment | 2DG4 | 2DG4 + Cef | 1% |
| no pretreatment | 2DG4 | 2DG4 + AgNO3 + Cef | 30% |
| no pretreatment | 2DG4 + AgNO3 | 2DG4 + AgNO3 + Cef | 55% |
| 2DG4 + AgNO3 (1 day) | 2DG4 + AgNO3 | 2DG4 + AgNO3 + Cef | 43% |
| 2DG4 + AgNO3 (4 days) | 2DG4 + AgNO3 | 2DG4 + AgNO3 + Cef | 27% |
| 2DG4 (6 days) | 2DG4 + AgNO3 | 2DG4 + AgNO3 + Cef | 65% |
| 2DG4 (6 days) + 1 day on 2DG4 + AgNO3 | 2DG4 + AgNO3 | 2DG4 + AgNO3 + Cef | 88% |

TABLE 3

Inoculation of maize type I callus
Type I calli are inoculated with Agrobacterium LBA4404 (GIGUP) ($10^9$ cells/ml). The basic medium used in these experiments is 2DG4 + 0.52, 4D (2DG4) with or without silver nitrate (AgN03). All experiments are done on about 150 pieces of type I callus. Survival of tissues is scored 2 weeks after inoculation.

| Type I callus | pretreatment | Co-inoculation | Transfer | Score |
|---|---|---|---|---|
| 1/2 month old | 2DG4 | 2DG4 + AgNO3 | 2DG4 + AgNO3 + Cef | 75% |
|  | 2DG4 + AgNO3 | 2DG4 + AgNO3 | 2DG4 + AgNO3 + Cef | 95% |
|  | 2DG4 | 2DG4 | 2DG4 + Cef | 22% |
| 10 month-old | 2DG4 | 2DG4 + AgNO3 | 2DG4 + AgNO3 + Cef | 55% |
|  | 2DG4 + AgNO3 | 2DG4 + AgNO3 | 2DG4 + AgNO3 + Cef | 12% |

Example 3

Transformation by Agrobacterium of Immature Zygotic Embryos and Isolation of Transformed Callus with the Use of Phosphinothricin, Hygromycin or Mannose as a Selection Agent.

Immature embryos are obtained approximately 10 to 14 days after self-pollination. The immature zygotic embryos are divided among different plates containing medium capable of inducing and supporting embryogenic callus formation at about 25 immature embryos per plate.

The immature embryos are inoculated either on the plate or in liquid as indicated in example 2 with Agrobacterium having a Ti plasmid comprising a selectable marker gene. Through a series of experiments, optimized conditions are developed for immature embryos. In one optimized condition, the immature embryos are plated on callus initiation medium containing silver nitrate (10 mg/l) either prior or immediately after inoculation with Agrobacterium. Approximately 25 immature embryos are placed onto each plate. 16 to 72 hours after inoculation, immature embryos are transferred to callus initiation medium with silver nitrate and cefotaxim. Selection of transformed cells is carried out as follows:

a. PPT resistance marker: Transformation is carried out using an Agrobacterium strain harboring a plasmid with a gene coding for resistance to phosphinothricin on the T-DNA region. Transformed cells are selected in vitro by application of phosphinothricin at a concentration of 3 mg/L 2 to 20 days after inoculation and maintained for a total of 2–12 weeks. The embryogenic callus so obtained is regenerated in the presence or absence of phosphinothricin on standard medium of regeneration. All plants are tested by the chlorophenol red (CR) test for resistance to PPT. This assay utilizes a pH sensitive indicator dye to show which cells are growing in the presence of PPT. Cells that grow produce a pH change in the media and turn the indicator Chlorophenol Red yellow (from red). Plants expressing the resistance gene to PPT are easily identified in this test. Plants positive by the CR test are assayed by PCR for the presence of the PAT gene. Plants which are positive for PCR test are analyzed by Southern blot.

b. Hygromycin resistance marker: Transformation is carried out using an Agrobacterium strain harboring a plasmid with a gene (hpt, hygromycin B phosphotransferase) coding for resistance to hygromycin on the T-DNA region. Transformed cells are selected using hygromycin at a concentration of 3 mg/L 2 to 20 days after inoculation and maintained for a total of 2–12 weeks. The embryogenic callus so obtained is regenerated in the presence or absence of the selectable agent on standard medium of regeneration. All plants are tested for resistance to hygromycin. Plants expressing the resistance gene to hygromycin are easily identified in this test. Plants positive by this test are assayed by PCR for the presence of the hpt gene. Plants which are positive by PCR test are analyzed by Southern blot.

c. Positive selection with mannose: Transformation is carried out using an Agrobacterium strain harboring a plasmid with a gene (mannose phosphate isomerase) coding for tolerance to mannose on the T-DNA region, mannose is used to select transformed cells in vitro. This selection can be applied as low as 1 g/L 2 to 20 days after inoculation and maintained for a total of 2–12 weeks. The embryogenic callus so obtained can be regenerated in the presence or absence of mannose on standard medium of regeneration. All plants are tested by the chlorophenol red (CR) test for tolerance to mannose. This assay utilizes a pH sensitive indicator dye to show which cells are growing in the presence of mannose. Cells that grow produce a pH change in the media and turn the indicator Chlorophenol Red yellow from red. Plants expressing the tolerance to mannose are easily identified in this test. Plants positive by the CR test are assayed by PCR for the presence of the mannose gene. Plants which are positive for PCR test are analyzed by Southern blot.

Example 4

Transformation by Agrobacterium of Callus Derived from Immature Zygotic Embryos and Isolation of Transformed Callus with the Use of Phosphinothricin, Hygromycin and Mannose as Selectable Agents Type I callus is obtained from immature zygotic embryos using standard culture techniques. Approximately 25 pieces of type I callus are placed on maintenance medium containing silver nitrate either prior or after inoculation with Agrobacterium. The inoculation may be performed as described in example 2. Approximately 16–72 hours after inoculation the callus is transferred to standard culture medium containing silver nitrate and cefotaxim. The selection can be applied immediately after transfer on this medium or 1 to 20 days after. The callus is then subcultured on selection for approximately 2 to 12 weeks, after which surviving and growing callus is transferred to standard regeneration medium for the production of plants.

Selection is carried out as in the preceding example for cells transformed with genes for phophinothricin resistance, hygromycin resistance, or mannose phosphate isomerase.

Example 5

Transformation of Type I Callus of Maize by Inoculation with Agrobacterium and Isolation of Transformed Callus with the Use of Phosphinothricin, Hygromycin and Mannose as Selectable Agents.

Callus is derived from plating immature embryos of elite genotype. Cultures are subcultured bimonthly on maintenance medium(2DG4+0.5 mg/l 2,4-D) and cell clumps taken 2–3 days after subculture are placed on 2DG4 medium. After or prior inoculation with Agrobacterium, cell clumps are plated on 2DG4 medium containing silver nitrate. Inoculation with Agrobacterium may be performed as described in example 2. After 16 to 72 hours incubation, the callus is transferred to fresh maintenance medium containing cefotaxim and silver nitrate. The callus is subcultured on selection for a total approximately 2–12 weeks with the selectable agent, after which surviving and growing callus is transferred to standard regeneration medium for the production of plants. Selection is carried out as in the preceding example for cells transformed with genes for phophinothricin resistance, hygromycin resistance, or mannose phosphate isomerase.

Example 6

Heat Shock Treatment Prevents Apoptosis Triggered by Agrobacterium

Immature Embryos:

Maize inbred lines are grown in the greenhouse. Immature embryos (0.8 to 2.2 mm in length) are aseptically excised from surface-sterilized ears between 8 and 15 days after pollination, depending upon environmental factors.

Embryos are plated scutellum up on callus initiation medium. For most of the inbred lines, the embryos are plated on LS medium (Linsmaier and Skoog, Physiol. Plant. 18: 100–127, 1965). Embryos of CG00526 are plated on 2DG4+5 mg/l chloramben (2DG4–5 Chl). 2DG4 medium is Duncan's medium modified to contain 20 mg/l sucrose (Koziel et al., Bio/Technology 11: 194–200, 1993).

Type I Callus:

Immature embryos are sterilized as described above and plated on callus initiation medium (2DG4–5 Chl) and cultured therein for 1 to 7 days. Embryos plated on callus initiation medium (2DG4+5 Chl) for 7 to 20 days give rise to callus. These calli are typical type I calli. Type I calli were compact clusters of relatively well organized cells. Resultant embryogenic callus is cut from the embryos and transferred to callus maintenance medium, 2DG4+0.5 mg/l 2,4-dichlorophenoxy acetic acid (2,4-D) and used for inoculation. Type I callus obtained by the method described above can be maintained on the maintenance medium (2DG4+2,4 D 0.5 mg/l) and subcultured approximately every 2 weeks.

Agrobacterium:

The strain used is A. tumefaciens LBA4404 (pAL4404, pSB1). pAL4404 is a disarmed helper plasmid (Ooms et al, 7:15–29,1982). pSB1 is a wide host range plasmid containing a region of homology to pGIGUP and a 15.2 kb Kpnl fragment from the virulence region of pTiBo542 (Ishida et al, Nature Biotechnology 14: 745–750, 1996). The introduction of the plasmid pGIGUP by electroporation into LBA4404(pAL4404, pSB1) resulted in a cointegration of pGIGUP and pSB1. pGIGUP contains a plant expressible phosphinothricin acetyl transferase (PAT) gene driven by the maize ubiquitin promoter to provide resistance to phosphinothricin (Christensen et al, Plant Mol. Biol. 18: 675–689, 1992). It also contains a gene for $\beta$-glucuronidase expression (GUS) with an intron in the N-terminal codon of the coding sequence driven by the chimeric promoter derived from the octopine and mannopine synthase genes (a trimer of the octopine synthase promoter upstream activating sequence with a domain of the mannopine synthase promoter, Ni et al, Plant J., 7: 661–676,1995). This intron-GUS gene expresses GUS activity in the plant cell but not in Agrobacterium. Agrobacterium is grown for 3 days on YP medium (5 g/l yeast extract, 10 g/l peptone, 5 g/l NaCl, 15 g/l agar, pH 6.8) supplemented with 50 mg/l spectinomycin and 10 mg/l tetracycline. Bacteria are collected with a loop and suspended in N6 liquid medium at a density ranging from $10^9$ to $5 \times 10^9$ cells/ml. Agrobacterium can alternatively be collected from an overnight culture in YP medium and resuspended in N6 liquid medium. It can also be pre-induced for 4 to 6 hrs in Agrobacterium Induction Medium (AIM; $K_2HPO_4$,10.5 g; $KH_2PO_4$, 4.5 g; $(NH_4)2SO_4$, 1.0 g; NaCitrate.$2H_2O$, 0.5 g; $MgSO_4.H_2O$ (1 M), 1.0 ml; Glucose, 2.0 g; Glycerol, 5.0 ml; MES (10 mM); Acetosyringone (50–100 $\mu$M); pH 5.6).

Heat Shock Treatment of Tissues:

Before cocultivation, maize tissues are placed in an Eppendorf tube in N6 liquid medium and incubated for 4 min at 45° C. in a water bath. The medium is then replaced by an Agrobacterium suspension prepared as described above. After 5 min at room temperature, tissues are plated on appropriate solid medium. 3 days after co-inoculation, tissues are either stained with X-Glu to detect GUS activity or plated on medium with cefotaxime (250 mg/l). Maize tissues are then examined to detect callus response indicating the percentage of tissues surviving Agrobacterium inoculation.

Cocultivation:

Maize tissues prepared as described above are inoculated with Agrobacterium. They are soaked in the bacterial suspension for 5–10 min and then plated on solid medium. After inoculation, maize tissues were cultured in the dark at 25° C. 2 or 3 days after inoculation, tissues are transferred onto the same medium supplemented with cefotaxime (250 mg/l).

In Situ Detection of DNA Fragmentation:

Embryos are soaked in a 3.7% formadehyde solution and processed as described by the manufacturer (Trevigen). To detect genomic DNA cleavage in situ, fixed embryos are treated with the TACS-1 kit (Cullivier et al., Nature 381: 800–803, 1996). Fixed cross-sections are first treated with proteinase K for 5 min at room temperature and then dipped for 5 min into 2% hydrogen peroxide to remove endogenous peroxidase. After a brief wash with klenow buffer, tissues are incubated for 1 hr at 37° C. with the klenow enzyme that can incorporate exogenous modified deoxynucleotides to the 5' termini of the cleaved fragments. A dark insoluble precipitate indicative of apoptosis that appears in the individual cell is detectable with a microscope.

Results:

A major browning phenomenon was observed following cocultivation of Agrobacterium and maize tissues and a concentration of $10^9$ cells/ml could induce cell death. Embryos appeared to be more sensitive to Agrobacterium than embryogenic callus.

Embryos and type I callus are heat shocked and then inoculated with Agrobacterium at a concentration of $10^9$ cells/ml. Following three days of co-cultivation and culture for a week, tissues are examined. The level of protection conferred by the heat shock pretreatment is quantified by counting the number of tissues that survive the inoculation.

All embryos inoculated with Agrobacterium after a heat shock pretreatment show callus initiation whereas no callus emerges from embryos that are not heat shocked (Table 4).

TABLE 4

Embryos are inoculated with $10^9$ cells/ml Agrobacterium LBA4404 (pGIGUP) and then plated on callus initiation medium. The basic medium is 2DG4 + 5Chl (2DG4). All treatments are done on about 80 to 100 embryos and repeated twice. Callus initiation is scored two weeks after inoculation.

| Pretreatment | Embryos with callus response/ Embryos inoculated |
|---|---|
| Control | 137/150 (91%) |
| No Heat Shock + Agro | 3/150 (2%) |
| Heat Shock + Agro | 112/150 (75%) |

The same beneficial effect of the heat shock treatment is observed for callus (Table 5).

TABLE 5

Type I callus is inoculated with $10^9$ cells/ml Agrobacterium LBA4404 (pGIGUP). The basic medium used is 2DG4 + 0.5 2,4D (2DG4). All experiments are performed on approximately 1000 pieces of Type I callus. Survival of tissues is scored 2 weeks after inoculation.

| Pretreatment | Survival Score |
|---|---|
| 3 month-old Type I callus line | |
| Agrobacterium | 0/1000 |
| Agro + heat shock | ≈1000/1000 |
| 10 month-old Type I callus line | |
| Agrobacterium | 0/1000 |
| Agro + heat shock | ≈1000/1000 |

The protection observed after heat shock pretreatment appears to be associated with heat shock because major heat shock proteins can be amplified by RT-PCR.

No DNA fragmentation is detected in embryos subjected to a heat shock pretreatment.

Embryos from various maize lines are inoculated with Agrobacterium strain LBA4404 (GIGUP) induced in AIM solution with or without a heat-shock pretreatment. After three days of co-cultivation, embryos are stained for GUS activity. Results are presented in Table 6. It appears that a heat shock pretreatment has a beneficial effect on transient expression.

TABLE 6

| Pedigree | Treatment | GUS pos. % of total* | GUS Rating** |
|---|---|---|---|
| 0F502 | — | 15 | 0.3 |
|  | HS | 74 | 1.8 |
| FNU007 | — | 90 | 2.0 |
|  | HS | 96 | 3.4 |
| HAF031 | — | 0 | 0.0 |
|  | HS | 67 | 0.9 |
| 2N217A | — | 13 | 0.1 |
|  | HS | 46 | 0.4 |
| 1NJ20 | — | 5 | 0.1 |
|  | HS | 38 | 0.4 |
| JEF091 | — | 59 | 1.2 |
|  | HS | 81 | 1.4 |

—: No heat shock.
HS: heat shock.
*GUS percentages are based on a sample size of approximately 50 immature embryos.
**GUS rating is based on a 0–5 scale (0 = no GUS stain, 1 = 1–5 spots/embryo, 2 = 5–15 spots, 3 = 15–30 spots, 4 = ~25% of the embryo surface staining for GUS and, 5 = ~50% of the embryo surface staining for GUS.

Example 7

Agrobacterium Transformation of Wheat

Immature zygotic embryos (0.75 mm to 1.25 mm) are excised and plated on MS-based medium with 3 mg/l 2,4-D, 300 mg/l glutamine, 150 mg/l asparagine and 3% sucrose (3MS3S) for 0, 3, 4, 5, 6, 7, 8 or 21 days before inoculation with Agrobacterium. By 21 days, the explants produce an embryogenic mass referred to as 3-week callus.

Cocultivation:

Wheat tissues are inoculated with the Agrobacteria described in Example 6. Wheat tissues are soaked in the bacterial suspension for 5–10 min and then plated on solid medium. After inoculation, wheat tissues are cultured in the dark at 25° C. 2 or 3 days after inoculation, tissues are transferred onto the same medium supplemented with cefotaxime (250 mg/l). The explants are inoculated without being given a pre-treatment or they are heat shocked at 42–48° C. for 4–8 minutes. The heat shock treatment is performed prior to inoculation. Embryos can be heat-shocked in 3MS inf or AIM with 100 mM AS liquid whereas calli are heat-shocked "dry".

Inoculation:

Explants are inoculated in either eppendorf tubes or on plates. When inoculating in tubes, 1 ml of the Agrobacterium solution is pipetted into the tube, finger-vortexed or shaken and allowed to sit for 5–15 minutes. The Agrobacterium solution and explant material is then poured onto a plate of 3MS3S with 100 mM AS and the liquid is removed with a disposable narrow-tipped transfer pipet. When inoculation is done on plates the Agrobacterium is pipetted directly onto the explants and removed 5–15 minutes later. Embryos are arranged so that the embryonic axes are in contact with the medium.

Callus Initiation, Selection and Regeneration:

Embryos are grown on callus induction medium (3MS3S) with antibiotic for 3 weeks. The embryogenic calli are dissected and placed on MS3S (no 2,4-D) with 5 mg/l $GA_3$ and 1 mg/l NAA with the selection agent and antibiotic for 2 weeks then removed to MS3S with antibiotic and a higher concentration of selection agent for approximately 4 weeks. The plantlets are then transferred to Magenta boxes with ½ MS salts and 0.5 mg/l NAA while keeping the concentration of the selection agent the same as the last step-up. For calli, the selection and regeneration system is the same except that the calli are grown only for a maximum of 6 weeks from embryo plating, that is, 3 week calli are inoculated, co-cultivated and grown for a maximum of 3 more weeks before selection and regeneration starts.

Results:

DNA fragmentation is studied in embryos inoculated with Agrobacterium as described in Example 6. No DNA fragmentation is detected in embryos subjected to a heat shock pretreatment.

Heat shock pretreatment prior to Agrobacterium inoculation can prevent the onset of apoptosis.

Example 8

Suppression of Agrobacterium-induced Apoptosis in Maize Cells by p35 and iap

Vectors for Biolistic Transformation:

Vectors used to transform maize by the biolistic device are all derivatives of pUC. pUbiPAT contains a plant expressible bar gene encoding for the phosphinothricin acetyl transfeerase (PAT) driven by the maize ubiquitin promoter (Christensen et al., 1992) to provide resistance to phophinothricin (PPT). The coding region of p35, iap and dad-1 are cloned under control of the maize metallothionein-like gene promotor (MTL) (de Framond, 1991). p35 and lap are provided by Lois Miller (University of Georgia, Athens, Ga.). The p35 PstI-EcoRI fragment encompassing the coding region is cut out of pHSP35VI+ (Clem and Miller, 1994), cloned into the corresponding sites of pBluescript (Stratagene, La Jolla, Calif.) and then cloned as a PstI-Asp718 fragment into the corresponding sites of pMTL. pMTL contains the MTL promoter and the CaMV35S terminator. The SalI-SpeI fragment encompassing the coding region of iap from pHSCpIAPVI+ (Clem and Miller, 1994) is cloned into XhoI-SpeI sites of pMTL. The coding sequence of dad-1 was cloned as a SalI-XbaI from the Arabidopsis cDNA clone 12T7 (University of Michigan).

Vectors for Agrobacterium Transformation:

p35, iap and dad-1 coding regions driven by the MTL promoter are cloned between the border sequences into the superbinary vector pSB11.

The β-glucuronidase gene (GUS) with an intron in the N-terminal codon of the coding sequence is driven by a chimeric promoter derived from the octopine and mannopine synthase genes (mas; trimer of the octopine synthase promoter upstream activating sequence with a domain of the mannopine synthase promoter; Ni et al., 1995). Mas-GUS expressing GUS activity in the plant cell but not in Agrobacterium is cloned into pSB11 to yield pMasGUS.

These vectors are then introduced into LBA4404 (pAL4404, pSB1) by electroporation with 0.2 cm Bio-Rad cuvettes at a field strength of 2 kV/cm, resistors of 600 Ohms and a capacitance of 25 µF. pSB1 is a wide host range plasmid that contains a region of homology to pSB11 and a 15.2 kb KpnI fragment from the virulence region of pTiBo542 (Ishida et al., 1996). The introduction of the plasmid pSB11 by electroporation into LBA4404(pAL4404, pSB1) results in a cointegration of pSB11 and pSB1.

Inoculation of Maize Embryos with Agrobacterium:

Immature embryos (0.8 to 2.5 mm) are aseptically excised 12 to 15 days after pollination and plated scutellum up on callus initiation medium (2DG4+5 Chloramben; Duncan et al., 1985). Embryos are inoculated with Agrobacterium at a density of $10^9$ cells/ml for 5 min and then cultured on the callus initiation medium for 3 days. Tissues are then transferred on the same medium supplemented with cefotaxime (250 mg/l). Survival of tissues is scored 2 weeks after inoculation.

Initiation of Type I Callus:

Embryos plated on callus initiation medium for 7 to 20 days give rise to callus. These calli are typical type I calli, which are compact clusters of relatively well organized cells (Suttie et al., 1994). Resultant embryogenic callus is cut out of embryos and transferred to callus maintenance medium, 2DG4+0.5 mg/l (2,4-dichlorophenoxy) acetic acid (2,4-D). Type I callus obtained by the method described above can be maintained on the maintenance medium (2DG4+2,4 D 0.5 mg/l) and subcultured every 2 weeks approximately. Type I callus is used for inoculation experiments with Agrobacterium and for transformation by the biolistic device.

Transformation Experiments:

Plasmid DNA is precipitated onto 0.3 to 1 µm gold microcarrier as described in the DuPont Biolistic manual. 2 µg of the anti-apoptotic gene and 2 µg of pUbiPAT are used per 50 µl of microcarrier. 16 pieces of type I callus per plate are bombarded using the PDS-1000/He biolistic device (DuPont). Tissues are placed on the shelf 8 cm below the stopping screen shelf and a 10×10 µm stainless steel screen is used with rupture discs of 650 psi value. After bombardment, tissues are cultured in the dark for one day at 25° C., then transferred to callus maintenance medium 2DG4+0.5 mg/l 2,4-D. 10 days later, tissues are transferred onto the same medium supplemented with 100 mg/l PPT. Six to eight weeks later, tissues are transferred onto 40 mg/l PPT. Some of the tissues are then used for inoculation experiments and some of it is transferred on regeneration medium (Murashige and Skoog containing 3% sucrose, 0.25 mg/l ancymitol and 5 mg/l kinetin) with 16 hours of light per day. Transformed plants are identified using the chlorophenol red (CR) assay to test for resistance to PPT (Cramer et al., 1993) and then confirmed by PCR.

Inoculation of Transgenic Type I Callus with Agrobacterium:

Trangenic type I tissues obtained as described above are inoculated with Agrobacterium. Maize tissues are soaked in the bacterial suspension for 5–10 min. After inoculation, maize tissues are cultured in the dark at 25° C. on 2DG4+0.5 mg/l 2,4-D. Two or three days after inoculation, tissues are transferred on the same medium supplemented with cefotaxime (250 mg/l).

Analysis of Transgenic Material:

Genomic DNA is extracted from 100 mg of callus with the Isoquick kit (Microprobre, CA) and resuspended in 20 µl water. 1 µl is used for PCR reaction. PCR reactions are performed in Perkin-Elmer thermal cyclers in a 25 µl reaction using 1× PCR buffer, 0.5 unit of AmpliTaq, 200 µM each dNTPs, 0.2 µM of each primer. To detect the presence of the pat gene in tissues, PCR reactions are performed with the PAT primers at an annealing temperature of 55° C. For iap, p35 and dad-1 gene detection in transgenic tissues, the primers used for each reaction are, P and I, P and 35, P and D at an annealing temperature of 55° C., 55° C., 48° C. respectively.

```
PAT1:      5'-TGTCTCCGGAGAGGAGACC-3'         (SEQ ID NO: 1)

PAT2:      5'-CCAACATCATGCCATCCACC-3'        (SEQ ID NO: 2)

MTL (P):   5'-AGGTGTCCATGGTGCTCAAG-3'        (SEQ ID NO: 3)

iap (I):   5'-ACAATCGAACCGCACACGTC-3'        (SEQ ID NO: 4)

p35 (35):  5'-CCAGGTAGCAGTCGTTGTGT-3'        (SEQ ID NO: 5)

dad-1 (D): 5'-CCTTGTTTCCTTTGTTCACT-3'        (SEQ ID NO: 6)
``` p35 and iap RT-PCR:

Total RNA is extracted from transgenic callus using Tripure Isolation Reagent (Boehringer Mannheim), treated with RNase-free DNase, and 0.5 µg is taken for cDNA synthesis using advantage RT-PCR (Clontech) and oligo-dT primer. After the second-strand synthesis, one twentieth of this reaction is used as a template for PCR reaction with Taq DNA polymerase.

p35 primers used for RT-PCR are:

5'-GGTCCTATACGAAGCGTTAC-3' (SEQ ID NO: 7) and 5'-CCACGTAGCAGTCGTTGTGT-3' (SEQ ID NO: 8) amplifying 300 bp of transcript.

iap primers used for RT-PCR are:

5'-CATGTCTGACTTGCGATTGG-3' (SEQ ID NO: 9) and 5'-ACAATCGAACCGCACACGTC-3' (SEQ ID NO: 10), amplifying 248 bp of transcript.

To exclude contamination of genomic DNA, control cDNA reactions in which reverse transcriptase is omitted are prepared in parallel.

Results:

Most of embryos and embryogenic calli do not survive the inoculation with Agrobacterium A short exposure (5 min) is sufficient to induce this reaction. Tissues that are cocultivated with *Escherichia coli* and subjected to the same procedures do not exhibit any damage.

p35, iap and dad-1 were cloned into plant expression cassette between the border sequences of the T-DNA. As these anti-apoptotic genes are carried by the T-DNA, they should be delivered to maize cells at the time of inoculation. Maize tissues are inoculated with Agrobacterium LBA4404 ($10^9$ cells/ml) with or without cell death suppressor genes (between brackets). Following cocultivation, maize embryos or type I callus are examined to quantify tissue survival as an indication of the level of protection conferred by the expression of the anti-apoptotic genes. All treatments are done on about 50 to 80 maize explants and repeated twice. Tissues are transferred 3 days after inoculation on the same medium containing cefotaxime. The effect of Agrobacterium is scored two weeks after inoculation. The results are presented in Table 7 and 8, respectively.

TABLE 7

(embryos)

| | No of tissues with response/ No of tissues tested (%) | |
|---|---|---|
| | Experiment #1 | Experiment #2 |
| No bacteria | 52/63 (82%) | 25/31 (80%) |
| LBA4404 | 2/55 (3%) | 3/89 (3%) |
| LBA4404 (p35) | 19/75 (25%) | 18/74 (24%) |
| LBA4404 (iap) | 22/89 (24%) | 21/75 (28%) |
| LBA4404 (dad-1) | 4/48 (8%) | 10/66 (15%) |

TABLE 8

(type I callus)

| | No of tissues with response/ No of tissues tested (%) | |
|---|---|---|
| | Experiment #1 | Experiment #2 |
| No bacteria | 76/80 (95%) | 72/80 (90%) |
| LBA4404 | 8/80 (10%) | 6/80 (7.5%) |
| LBA4404 (p35) | 23/80 (29%) | 27/80 (33%) |
| LBA4404 (iap) | 25/80 (31%) | 30/80 (37%) |
| LBA4404 (dad1) | 15/80 (18%) | 13/80 (16%) |

About 80% of embryos give rise to embryogenic calli when they are not treated with Agrobacterium. About 25% of embryos treated with Agrobacterium harboring either p35 or iap give rise to embryogenic callus whereas only 3% of embryos inoculated with Agrobacterium exhibited callus initiation. A similar effect is observed with Type I callus inoculated with Agrobacterium harboring p35 or iap (Table 2). dad-1 did only confer low levels of protection in any system.

It appears that transient expression of p35 and iap reduce the browning of tissues to some extent but do not completely inhibit the phenomenon. This can be explained by a low efficiency of T-DNA transfer into the maize cells. As judged by transient expression with GUS, it appears that the target tissue is not uniformly transformed. This can be an indication that very few cells are recipients of the T-DNA.

The structure of the embryogenic callus emerging from embryos inoculated with Agrobacterium containing p35 or iap are not as compact as the control ones. This can be explained by the fact that only cells receiving the T-DNA carrying the anti-apoptotic gene survive and that individual transformed cells do not necessarily transmit the signal to neighbour cells. This type of tissue growth can be evidence that the cell death suppressor genes rescue doomed cells very effectively but their short-term expression does not confer full protection against the effect of Agrobacterium.

Embryogenic calli transgenic for p35, iap and dad-1 result from delivery of said genes unter the control of a plant expressible promoter into Type I callus using microprojectile bombardment. The constructs are co-bombarded with the bar gene, tissues are selected on PPT and the transformed status of these callus is first confirmed by PCR (Table 9).

TABLE 9

| Transformation experiment | # PCR+ |
|---|---|
| UbiPAT | 5 PAT+ |
| MTLp35, UbiPAT | 9 PAT+, 3 p35+ |

TABLE 9-continued

| Transformation experiment | # PCR+ |
|---|---|
| MTLiap, UbiPAT | 7 PAT+, 5 iap+ |
| MTLdad, UbiPAT | 11 PAT+, 4 dad-1+ |

Sensitivity to Agrobacterium inoculation is then assayed on independent events. Callus is inoculated with Agrobacterium LBA4404 ($10^9$ cells/ml). Two independent transgenic callus lines are tested. All treatments are repeated twice. Tissues are transferred 3 days after inoculation on the same medium containing cefotaxime. Survival of maize tissues is scored two weeks after inoculation with Agrobacterium (Table 10).

TABLE 10

| | Number of resistant calli to LBA4404 | |
|---|---|---|
| Transformation experiment | Line 1 | Line 2 |
| UbiPAT | 1/24 (4%) | 1/32 (3%) |
| MTLp35, UbiPAT | 22/25 (88%) | 25/28 (89%) |
| MTLiap, UbiPAT | 20/22 (90%) | 19/25 (76%) |
| MTLdad, UbiPAT | 12/27 (44%) | 9/22 (41%) |

Embryogenic calli transgenic for p35 and iap do not exhibit cell death when subjected to Agrobacterium inoculation whereas a major browning phenomenon is observed on control tissues following cocultivation. The presence of dad-1 gene delays the onset of apoptosis but does not block cell death as well as iap and p35 do. The results are reproducible in several independent experiments.

The protective effect of p35 and iap is also evident when measured by oligonucleosomal DNA fragment electrophoresis.

It appears, that the effect of dad-1 is more obvious when stably expressed in the tissues.

There is a clear correlation between expression of the anti-apoptotic genes and the absence of cell death. p35 and iap genes are expressed in transgenic callus as judged by reverse-transcription-PCR (RT-PCR). Control were uniformly negative.

Example 9

Screening and Identification of Agrobacterium Strains Which Do Not Induce Cell Death in Maize Cells The sensitivity of embryogenic callus and embryos of a well studied maize line (A188) and a proprietary elite line (Elite 2) to various Agrobacterium strains is tested using a panel of 40 wild-type strains of Agrobacterium. These strains are first tested for their compatibility with A188 and Elite 2 embryogenic calli and embryos. Among those, 6 of the 40 strains do not entirely prevent the growth of maize tissues and are further tested on Elite 2 embryos plated on callus initiation medium and inoculated at a concentration of $10^9$ cells/ml. Callus initiation is scored 2 weeks after inoculation and expressed as a percentage of embryos with response.

These strains are also tested for their virulence on tobacco leaf discs plated on hormone-free medium, and it is noted that potential of the strains to induce programmed cell death in maize cells does not correlate with the virulence. The percentage in Table 11 describes the number of leaf discs with tumors.

TABLE 11

Comparison of virulence of non-necrogenic strains

| Strains | Source | Opine | Virulence tested on Tobacco (%) | 2DG4 + 5Chl (%) |
|---|---|---|---|---|
| 1 | rose | ? | 100 | 37 |
| 2 | peach | nopaline | 82 | 25 |
| 3 | silver poplar | agropine | 66 | 50 |
| 4 | chrysanthemum | L,L Sap | 100 | 63 |
| A | rose | nopaline | 92 | 66** |
| B | salix | nopaline | 76 | 58** |

**Good type I callus.
Agrobacterium strains A and B have been deposited with ATCC on May 2, 1997 under the Budapest Treaty under ATCC designation numbers 55964 and 55965 respectively.

Example 10

Agrobacterium Genes Triggering Apoptosis in Maize Cells

A BAC library (bacterial artificial chromosome) is constructed with Agrobacterium genomic DNA fragments of approximately 100–200 kb in an effort to identify genetic elements responsible for the cell death response in maize embryogenic tissues. The library is introduced into *Escherichia coli*. To check whether such background is suited for screening of the BAC library, *E.coli* containing the BIBAC vector alone is inocuated on maize embryos. *E. coli* is found not to induce a characteristic apoptotic response.

It is estimated that about 25 to 30 BAC clones with a 150–200 kb inserts are sufficient to cover the entire genome of Agrobacterium, assuming that Agrobacterium has a genome size fairly equivalent to *E. coli* ($4.6 \cdot 10^6$ bp). A relatively large number of clones (200) are hybridized with an Agrobacterium chromosomal probe (chvD) in order to test whether the BAC library made in *E. coli* is a clear representation of the Agrobacterium genome. Among 200 clones tested, 5 lighted up with the chvD probe (data not shown).

One challenge is that the genetic components from Agrobacterium might be silent in *E. coli*. Furthermore, additional factors from plants and/or Agrobacterium might be necessary for the expression of such a clone. Therefore, the BAC vector also contains an origin of replication functional in Agrobacterium and can be readily transformed into Agrobacterium in such a scenario.

Bacterial Growth:

Agrobacterium is grown for 3 days on YP medium (5 g/l yeast extract, 10 g/l peptone, 5 g/l NaCl, 15 g/l agar, pH 6.8) supplemented with 100 mg/l kanamycin when needed. Bacteria are collected with a loop and suspended in N6 liquid medium at a density ranging from $10^9$ to $5 \times 10^9$ cells/ml. Agrobacterium cells can also be collected from an overnight culture in YP medium and resuspended in N6 liquid medium.

*E.coli* DH10B is grown in LB medium (1% bacto-tryptone, 0.5% bacto-yeast extract, 170 mM NaCl, pH 7.0). After transformation, it is grown in SOC solution (2% bacto tryptone, 0.5% bacto yeast extract, 10 mM NaCl, 2.5 mM KCl, 10 mM $MgCl_2$, 10 mM $MgSO_4$, 20 mM glucose, pH 7.0).

Preparation of Genomic DNA from Agrobacterium:

LBA4404 strain is used for the construction of the library. The protocol, materials and reagents used are from the Imbed kit (Biolabs, USA). 4×10 ml of Agrobacterium cultures are grown overnight at 28° C. One hour prior to harvesting, 180 mg/ml of chloramphenicol is added to align the chromosomes. The cells are centrifuged at 800 g at 4° C. for 15 min and the pellet is air dried. Cells are pre-warmed in 0.5 ml of cell suspension solution (10 mM Tris-HCl, 20 mM NaCl, 100 mM EDTA, pH 7.2) to 42° C. before being embedded in agarose. Agrobacterium cells are embedded in agarose rods to carry out the degradation of the cell wall and deproteinisation avoiding shearing of the DNA. To embed the cells in agarose rods, the cells are mixed with an equal volume of 1% low melting point agarose in dd$H_2$O cooled down to 42° C. and then allowed to harden in a Gel Syringe mold. Upon solidification of the agarose, the plugs are transferred to 3 volumes of lysozyme solution (1 mg/ml lysozyme, 10 mM Tris-HCl, 50 mM NaCl, 100 mM EDTA, 0.2% sodium deoxycholate, 0.5% N-laurylsarcosine, pH 7.2) and incubated for 2 hours at 37° C. with gentle shaking. The lysozyme solution is removed and the rods are washed twice with 3 ml wash solution for 15 min at a time. The rods are then incubated in 3 ml Proteinase K solution (1 mg/ml proteinase K, 100 mM EDTA, 1% N-laurylsarcosine, 0.2% sodium deoxycholate, pH 8.0) for 20 hours at 42° C. with gentle shaking. The Proteinase K solution is removed by aspiration and the rods are dialyzed twice against 5 ml wash solution (20 mM Tris-HCl, 50 mM EDTA, pH 8.0) for 15 min, then with 3 ml PMSF solution (20 mM Tris-HCl, 50 mM EDTA, 1 mM phenyl methyl sulfonyl fluoride, pH 8.0) for one hour, followed by two washes with wash solution. The rods are then washed twice with 5 ml storage solution (2 mM Tris-HCl, 5 mM EDTA, pH 8.0) for 15 min and then are reloaded into GelSyringes. Samples 1 mm in length (10–20 ml) are cut with a razor blade and dialyzed against NotI restriction endonuclease buffer (Biolabs, USA) for 30 min at 4° C. The restriction endonuclease buffer is replaced with fresh buffer and incubation is performed overnight at 37° C. with 20 units of NotI enzyme (Biolabs, USA). Partial digestion of the Agrobacterium DNA is achieved by using NotI, a rare cutting enzyme. NotI theoretically generates fragments 18 kb in length after a total digestion assuming the Agrobacterium genome has a G/C content of 60% (results extrapolated from different Agrobacterium genes). Aliquots are then loaded with a pipette whose tip is cut off. The DNA is separated by pulse field gel (PFG) electrophoresis on a 1% agarose gel in 0.5×TBE at 14° C. using a Bio-Rad CHEF Mapper at 6 V/cm for 32 h. The gel is stained for 20 min in 1 mg/ml EtBr dd$H_2$O bath and agarose slices containing fragments corresponding to 100–200 kb are excised from the gel. The agarose slices are dialysed twice against TE for one hour at 4° C. and twice with agarase buffer (Biolabs, USA) for one hour at 4° C., melted at 65° C. for 10 min and digested with one unit of agarase (Biolabs, USA) per 100 mg of agarose. The DNA concentration is estimated fluorometrically using the DyNA Quant 200 (Hoefer, USA).

Preparation of the BIBAC Vector:

The BIBAC vector was kindly provided by Dr. Carol M. Hamilton (Cornell University, Ithaca) (Hamilton et al., Proc. Natl. Acad. Sci. (USA) 93, 9975–9979, 1996). BIBAC is designed to replicate both in *E.coli* and Agrobacterium and it also contains the sacBll gene allowing direct selection for cloned inserts on a sucrose medium. BIBAC vector also harbors the F-factor episome's origin which allows stable maintenance of one or two copies per cell with up to 300 kb inserts (Shizuya et al., Proc. Natl. Acad. Sci. (USA) 89, 8794–8797, 1992). The plasmid is isolated using Wizard® Plus Maxiprep kit (Promega, USA). A phenol-chloroform extraction is performed before isopropanol precipitation. The plasmid is digested with NotI and dephosphorylated with 1 unit of shrimp alkaline phosphatase (Boerhinger Mannheim) at 37° C. for one hour. The ligation is carried out in 40 ml in which 150 ng of Agrobacterium DNA is incubated with 17 ng of cut vector (estimated molar ratio 10:1 with vector in excess) with 400 units of T4 DNA ligase (Boerhinger) at 17° C. overnight. Before transformation, the ligation is dialysed against TE and 1/10 TE in Micro-Collodion bags (Sartorius, Germany) at 4° C. for 2 hours.

Transformation of DH10B with pBAC Library

Transformation of competent E. coli DH10B cells (F, rec A1; ElectroMax, Gibco-BRL, USA) is carried out by electroporation in pre-cooled Gene Pulser cuvettes (Bio-Rad, USA) with Gene Pulser™ (Bio-Rad, USA) using the following settings: voltage 2.5 kV, capacitance 25 mF, and resistance 200 W. 25 ml of competent cells are mixed with 1 ml of ligation solution for each electroporation. After electroporation, cells are transferred to 0.5 ml SOC solution and incubated at 37° C. in a rotating wheel for 45 min. 150 ml aliquots of cells are plated on LB medium containing kanamycin (40 mg/ml) and sucrose (5%).

Isolation of BAC DNA and Determination of DNA Insert Size of BAC Clones

BAC clones are grown overnight under continuous agitation in 10 ml LB with kanamycin (50 mg/ml). DNA is extracted according to the alcaline lysis method (Sambrook et al., 1989) with the following modifications: RNAse 30 mg/ml is added to the resuspension solution and one phenol-chloroform purification is performed before isopropanol precipitation. The pellet of nucleic acid is dissolved in 50 ml of ddH$_2$O. The DNA is separated by PFG electrophoresis on a 1% agarose gel in 0.5×TBE at 14° C. using a Bio-Rad CHEF Mapper at 6 V/cm for 32 h.

Inoculation of Maize Embryos with Agrobacterium:

Immature embryos (0.8 to 2.5 mm) are aseptically excised 12 to 15 days after pollination and plated scutellum up on callus initiation medium (2DG4+5 Chloramben) (Duncan's "D" medium with glucose: N6 major, B5 minor, MS iron, 20 g/l sucrose 5 mg/l chloramben, 8 g/l purified agar, G4 additions and 10 mg/l glucose, pH 5.8) (Duncan et al., 1985). Bacteria cells are resuspended into 2N63SM (3.97 g/l N6 salts, N6 vitamins, 30 g/l sucrose, 2 mg/l 2,4-D, 8 g/l purified agar, pH 5.8). Embryos are inoculated with Agrobacterium or with E.coli at a density of $10^9$ cells/ml for 5 min and then cultured on the callus initiation medium for 3 days. Tissues are then transferred on the same medium supplemented with cefotaxime (250 mg/l). Survival of tissues is scored 2 weeks after inoculation.

Transformation of Agrobacterium

Agrobacterium transformation is performed as described previously (Wen-Jun and Forde, Nucleic. Acids Research 20: 8385, 1989) in a 0.2 cm electroporation cuvette (Bio-Rad Laboratories Ltd., USA) using a Gene Pulser™ (Bio-Rad, USA) at a field strength of 10 kV/cm (2.00 kV), a capacitance of 25 mF and a resistance of 600 Ω.

Vectors for Biolistic Transformation:

Vectors used to transform maize by the biolistic device are all derivatives of pUC. pMTL is a plant transformation vector containing the maize metallothionein-like gene promoter (MT-L) (de Framond, 1991). The coding region of virB1 is amplified by polymerase chain reaction with the BAC clone as a template and from strain A with the following primers: 5'-GGAGAGGCGGTGTTAGTT-3' (SEQ ID NO: 11); 5'-CATCATCGCATTCGAGAG-3' (SEQ ID NO: 12). PCR reactions are performed in Perkin-Elmer thermal cyclers, in a 25 μl reaction with 1× PCR buffer, 0.5 unit of AmpliTaq, 200 μM each dNTPs, 0.2 μM of each primer at an annealing temperature of 55° C. The PCR product is first cloned into the pCR2.1 vector for TA cloning (Invitrogen, San Diego, USA). It is then excised by an XbaI-SpeI double digestion and then cloned into the XbaI site of the pMTL vector in sense and antisense orientation giving rise to pMTL-virB1 and pMTL-virB1 as respectively. Similarly, the PCR product amplified from strain A is cloned into pMTL in sense and antisense orientation giving rise to pMTL-virB1A and pMTL-virB1A as respectively. acvB is cloned into the XbaI-XhoI site of pMTLsense and pMTLantisense, giving rise to pMTL-acvB and pMTL-acvBas.

pGUS contains the β-glucuronidase gene (GUS) with an intron in the N-terminal codon of the coding sequence and is driven by a chimeric promoter derived from the octopine and mannopine synthase genes (trimer of the octopine synthase promoter upstream activating sequence with a domain of the mannopine synthase promoter) (Ni et al., 1995).

Maize Suspension Cells

A suspension culture of Zea Mays cv Black Mexican Sweet (BMS) is maintained in N6 medium (Chu et al., 1975) and supplemented with 30 g/l sucrose and 2 mg/l 2,4-dichlorophenoxy acetic acid (2,4-D) (2N63S). Maize cell suspensions used for bombardment experiments are taken from 3 day-old rapidly growing cultures. Before bombarding, approximately 0.5 ml of packed volume cells is vacuum filtered onto 7-cm filters (Whatman, N°4). Plated cells are kept 4 hours at 25° C. on phytagar-solidified 2N6 medium containing 120 g/l sucrose prior to bombardment.

Bombardment of Plant Cells

Tissues are bombarded with gold microprojectiles onto which a mixture of plasmids is precipitated. pGUS plasmid DNA is used as an internal control in transient expression studies. For co-transformation experiments, the gold particles carry an equal mass of all plasmid DNAs (0.5 μg of each plasmid DNA per target plate). Appropriate quantities of each DNA are mixed in a total volume of 10 μl and precipitated with 50 μl of 2.5 M $CaCl_2$ and 20 μl of 0.1 M spermidine-free base onto 50 μl of 0.3 μm gold microcarriers (60 mg/ml). Microprojectile bombarment is performed with the PDS-1000 He biolistic device (DuPont) using 1100 psi rupture discs with the sample positioned 8 cm below the stopping screen shelf.

Transient Expression Assays

β-glucuronidase activity is determined by a chemoluminescent assay with the GUS-Light kit (Tropix). β-glucuronidase activities are expressed as light units detected by an Analytical Luminescence model 2001 Luminometer integrated over 10 seconds at 25° C.

Colony Hybridization

One day old BAC clones are lifted onto nylon filters (Hybond-N, Amersham Life Sciences, UK) for hybridization with radioactive labeled Agrobacterium derived probes. DNA probes are labeled with [a-$^{32}$P]dCTP using the oligo labeling kit of Pharmacia. The chvG probe and vitD1 probe corresponded to a PCR amplified fragment. The library filters are prehybridized in hybridization solution at 65° C. for two hours (5×SSPE, 5×Denhardt's solution, 0.5% SDS 0.1 mg/ml salmon sperm DNA). Hybridization is performed in the same buffer at 65° C. overnight. The filters are rinsed in 1×SSC, 0.1% SDS for 15 min at 65° C., followed by an incubation in 0.1×SSC, 0.1% SDS for 15 min at 65° C. The filters are briefly blotted dry, and film is exposed overnight at −70° C. using an intensifying screen. For PCR amplification, a loop of LBA4404 is resuspended in ddH$_2$O, heated at 95° C. for 15 min, centrifuged and 1 ml is used for PCR reaction with the following conditions: 5 min at 95° C., and then 30 cycles at 95° C. for 45 seconds, at 55° C. for 45 seconds, and at 72° C. for 45 seconds.

Results

Approximately 20 maize embryos are inoculated with one clone from the BAC library and plated on a callus initiation medium. Following co-cultivation, the embryos are transferred onto the same medium supplemented with 250 mg/ml cefotaxime. Embryos are then examined to assess damage caused by the recombinant bacterium. Among 160 clones screened 4 independent BAC clones are identified (BAC1, BAC2, BAC3, BAC4).

To further localize the region on the BAC clone responsible for the cell death of maize tissues, HindIII fragments from BAC clones are subcloned into a bluescript vector. Each of these clones are tested on maize tissues in order to determine which one retains the ability to elicit cell death.

The DNA sequences are determined by using subclones and oligonucleotides. The sequences of BAC1-2, BAC2-2 and BAC3-2 reveal homology with virB1, xylA-xylB and acvB respectively. BAC-4 is identical to BAC3-2.

BAC clones harboring acvB (BAC3 and BAC4), virB1 (BAC1) and xylA-xylB (BAC2) are introduced into strain A resulting in strains A(acvB), A(virB1) and A(xylA). These strains are used to inoculate maize tissues. Tissues inoculated with LBA4404 display a typical cell death pattern whereas the infection with strain A fails to produce these symptoms. A(acvB), A(virB1) and A(xylA) induce cell death at different levels, with A(acvB) being the strongest one. The presence of these genes thus converts the interaction of strain A with maize and renders the maize tissues more sensitive to infection (Table 12).

TABLE 12

| Strains | Exp 1 | Exp 2 | Exp 3 |
|---|---|---|---|
| No Bacteria | 19/22 (86%) | 15/18 (83%) | 16/18 (88%) |
| LBA4404 | 2/20 (10%) | 1/17 (6%) | 3/20 (15%) |
| *E. coli* | 17/20 (85%) | 16/19 (84%) | 17/21 (81%) |
| Strain A | 19/20 (95%) | 17/21 (81%) | 17/20 (85%) |
| *E. coli* (BAC1) | 5/20 (25%) | 5/17 (30%) | 4/18 (22%) |
| *E. coli* (BAC2) | 10/19 (52%) | 10/20 (50%) | 9/19 (47%) |
| *E. coli* (BAC3) | 3/18 (16%) | 4/17 (24%) | 3/20 (15%) |
| *E. coli* (BAC4) | 4/19 (21%) | 3/19 (16%) | 2/21 (9%) |
| Strain A (BAC1) | 5/19 (26%) | 6/17 (35%) | 8/25 (32%) |
| Strain A (BAC2) | 9/22 (41%) | 10/23 (43%) | 8/19 (42%) |
| Strain A (BAC3) | 3/20 (15%) | 2/18 (11%) | 3/21 (14%) |
| Strain A (BAC4) | 2/20 (10%) | 3/19 (16%) | 4/20 (20%) |

In Southern analysis, HindIII-digested genomic DNA from Agrobacterium strains A136, LBA4404, LBA4402, A, and B is probed under conditions of moderate stringency with either the fragment carrying xylA or acvB. Homologous fragments to xylA are present in all strains tested. Sequences hybridizing with acvB are found in LBA4404, LBA4402 and A136 that induce cell death in maize cells. Of interest, acvB is lacking in Agrobacterium strains A and B. acvB is thus limited in its distribution. As previously reported, acvB is present in relatively few strains of Agrobacterium (Wirawan et al., Biosci. Biotech. Biochem. 60: 44–49, 1993). xylA and acvB are not carried by the Ti plasmid because they were present on the Ti-cured strain LBA4402.

To determine whether expression of acvB and virB1 within maize cells is lethal, these genes are cloned into a plant expression vector and co-transformed with the pGUS vector expressing β-glucuronidase (GUS). In case the test gene is lethal, GUS activity is reduced or eliminated (Mindrinos et al., 1994). The coding region of the two genes is subcloned in sense and antisense orientation into a plant expression vector containing the MTL promoter and biolitistically delivered into maize cells along with the vector pGUS. After 30 hr the activity of GUS is assessed in maize cells. Results are shown in Table 13. The GUS activity is reduced about two fold when virB1 is co-bombarded with pGUS. Maize cells co-bombarded with acvB and pGUS consistently show a 35-fold reduction in GUS activity. This indicates that the expression of acvB at high levels within maize cells is deleterious.

TABLE 13

The plasmid constructs are delivered to maize cells by the biolistic device. Following incubation for 30 hr, tissues are homogenized and GUS activities are determined. Activities are expressed as Light Units/μg protein. Independent bombardments are analyzed, and data are presented as mean values of five repetitions ± SD.

| Plasmids + pGUS | Mean ± SD (Light Units/μg protein) |
|---|---|
| pUC | 2082 ± 199 |
| pMTL-virB1 | 1014 ± 106 |
| pMTL-virB1as | 2543 ± 176 |
| pMTL-virB1K6 | 1738 ± 330 |
| pMTL-virB1K6as | 2168 ± 282 |
| pMTL-acvB | 61 ± 19 |
| pMTL-acvBas | 2378 ± 292 |

What is claimed is:

1. A method for transforming a plant cell or tissue with a gene construct, comprising heat shocking said plant cell or tissue before co-cultivating with Agrobacterium, wherein said heat shock treatment inhibits Agrobacterium induced necrosis in said plant cell or tissue, and said Agrobacterium comprises a vector comprising said gene construct.

2. A method for producing a fertile transgenic plant comprising a gene construct, which method comprises:

(a) transforming a plant cell or tissue comprising heat shocking said plant cell or tissue before co-cultivating with Agrobacterium, wherein said heat shock treatment inhibits Agrobacterium induced necrosis in said plant cell or tissue and said Agrobacterium comprises a vector comprising said gene construct; and (b) regenerating the transformed plant cell or tissue to produce said fertile transgenic plant.

3. The method according to claim 1 or 2, wherein said plant cell or tissue is a gramineceous plant cell or tissue.

4. The method according to claim 3, wherein said plant cell or tissue is a maize cell or tissue.

5. The method according to claim 3, wherein said plant cell or tissue is a wheat cell or tissue.

6. The method according to claim 1 or 2, wherein said plant tissue is an embryogenic callus.

7. The method according to claim 1 or 2, wherein said plant tissue is an immature embryo.

8. The method according to claim 1 or 2, wherein said plant cell or tissue is heat shocked for 2 to 10 minutes.

9. The method according to claim 8, wherein said plant cell or tissue is heat shocked for 4 to 8 minutes.

10. The method according to claim 1 or 2, wherein said plant cell or tissue is heat shocked at 40° C. to 50° C.

11. The method according to claim 10, wherein said plant cell or tissue is heat shocked at 42° C. to 48° C.

12. A method for transforming a maize cell or tissue with a gene construct, comprising heat shocking said maize cell or tissue before co-cultivating with Agrobacterium, wherein said heat shock treatment inhibits Agrobacterium induced necrosis in said maize cell or tissue, and said Agrobacterium comprises a vector comprising said gene construct.

13. A method for producing a fertile transgenic maize plant comprising a gene construct, which method comprises:
    (a) transforming a maize cell or tissue comprising heat shocking said maize cell or tissue before co-cultivating with Agrobacterium, wherein said heat shock treatment inhibits Agrobacterium induced necrosis in said maize cell or tissue, and said Agrobacterium comprises a vector comprising said gene construct; and
    (b) regenerating the transformed maize cell or tissue to produce said fertile transgenic maize plant.

14. A method for transforming a plant cell or tissue with a gene construct, comprising exposing said plant cell or tissue to Agrobacterium under conditions which inhibit Agrobacterium induced necrosis, wherein said conditions comprise delivering to or expressing in said plant cell or tissue a nucleotide sequence comprising a coding sequence of a p35, iap or dad-1 gene, said delivery or expression of said nucleotide sequence inhibits Agrobacterium induced necrosis in said plant cell or tissue, and said Agrobacterium comprises a vector comprising said gene construct.

15. A method for producing a fertile transgenic plant comprising a gene construct, which method comprises:
    (a) transforming a plant cell or tissue comprising exposing said plant cell or tissue to Agrobacterium under conditions which inhibit Agrobacterium induced necrosis, wherein said conditions comprise delivering to or expressing in said plant cell or tissue a nucleotide sequence comprising a coding sequence of a p35, iap or dad-1 gene, said delivery or expression of said nucleotide sequence inhibits Agrobacterium induced necrosis in said plant cell or tissue, and said Agrobacterium comprises a vector comprising said gene construct; and
    (b) regenerating the transformed plant cell or tissue to produce said fertile transgenic plant.

16. The method according to claim 14 or 15, wherein said plant cell or tissue is a gramineceous plant cell or tissue.

17. The method according to claim 16, wherein said plant cell or tissue is a maize cell or tissue.

18. The method according to claim 16, wherein said plant cell or tissue is a wheat cell or tissue.

19. The method according to claim 14 or 15, wherein said plant tissue is an embryogenic callus.

20. The method according to claim 14 or 15, wherein said plant tissue is an immature embryo.

21. The method according to claim 14 or 15, wherein said coding sequence comprises a synthetic nucleotide sequence comprising codons which are preferred by the host plant.

22. The method according to claim 14 or 15, wherein said nucleotide sequence is transiently expressed.

23. The method according to claim 14 or 15, wherein said nucleotide sequence is expressed by a gene construct stably incorporated in the genome of said plant cell or tissue.

24. A method for transforming a maize cell or tissue with a gene construct, comprising exposing said maize cell or tissue to Agrobacterium under conditions which inhibit Agrobacterium induced necrosis, wherein said conditions comprise delivering to or expressing in said maize cell or tissue a nucleotide sequence comprising a coding sequence of a p35, iap or dad-1 gene, said delivery or expression of said nucleotide sequence inhibits Agrobacterium induced necrosis in said maize cell or tissue, and said Agrobacterium comprises a vector comprising said gene construct.

25. A method for producing a fertile transgenic maize plant comprising a gene construct, which method comprises:
    (a) transforming a maize cell or tissue comprising exposing said maize cell or tissue to Agrobacterium under conditions which inhibit Agrobacterium induced necrosis, wherein said conditions comprise delivering to or expressing in said maize cell or tissue a nucleotide sequence comprising a coding sequence of a p35, iap or dad-1 gene, said delivery or expression of said nucleotide sequence inhibits Agrobacterium induced necrosis in said maize cell or tissue, and said Agrobacterium comprises a vector comprising said gene construct; and
    (b) regenerating the transformed maize cell or tissue to produce said fertile transgenic maize plant.

26. A method for transforming a gramineceous plant cell or tissue with a gene construct, comprising exposing said plant cell or tissue to Agrobacterium under conditions which inhibit Agrobacterium induced necrosis, wherein said conditions comprise culturing said plant cell or tissue in a necrosis inhibiting medium, said necrosis inhibiting medium comprises (i) an ethylene inhibitor other than silver nitrate, or (ii) an ethylene synthesis inhibitor, and said Agrobacterium comprises a vector comprising said gene construct.

27. A method for producing a fertile transgenic gramineceous plant comprising, a gene construct, which method comprises:
    (a) transforming a gramineceous plant cell or tissue comprising exposing said plant cell or tissue to Agrobacterium under conditions which inhibit Agrobacterium induced necrosis, wherein said conditions comprise culturing said plant cell or tissue in a necrosis inhibiting medium, said necrosis inhibiting medium comprises (i) an ethylene inhibitor other than silver nitrate, or (ii) an ethylene synthesis inhibitor, and said Agrobacterium comprises a vector comprising said gene construct; and
    (b) regenerating the transformed plant cell or tissue to produce said fertile transgenic gramineceous plant.

28. The method according to claim 26 or 27, wherein said gramineceous plant cell or tissue is a maize cell or tissue.

29. The method according to claim 26 or 27, wherein said gramineceous plant cell or tissue is a wheat cell or tissue.

30. The method according to claim 26 or 27, wherein said gramineceous plant tissue is an embryogenic callus.

31. The method according to claim 26 or 27, wherein said gramineceous plant tissue is an immature embryo.

32. The method according to claim 26 or 27, wherein said necrosis inhibiting medium comprises 2,5-norbornadiene, norbornene, silver thiosulfate, aminoethoxyvinylglycine, cobalt salts, acetyl salicylic acid, or salicylic acid.

33. A method for transforming a maize cell or tissue with a gene construct, comprising exposing said maize cell or tissue to Agrobacterium under conditions which inhibit Agrobacterium induced necrosis, wherein said conditions comprise culturing said maize cell or tissue in a necrosis inhibiting medium, said necrosis inhibiting medium comprises (i) an ethylene inhibitor other than silver nitrate, or (ii) an ethylene synthesis inhibitor, and said Agrobacterium comprises a vector comprising said gene construct.

34. A method for producing a fertile transgenic maize plant comprising a gene construct, which method comprises:
  (a) transforming a maize cell or tissue comprising exposing said maize cell or tissue to Agrobacterium under conditions which inhibit Agrobacterium induced necrosis, wherein said conditions comprise culturing said maize cell or tissue in a necrosis inhibiting medium, said necrosis inhibiting medium comprises (i) an ethylene inhibitor other than silver nitrate, or (ii) an ethylene synthesis inhibitor, and said Agrobacterium comprises a vector comprising said gene construct.; and
  (b) regenerating the transformed maize cell or tissue to produce said fertile transgenic maize plant.

35. A transgenic plant, plant tissue or plant cell comprising a nucleotide sequence of heterologous origin which comprises a coding sequence of a p35, iap or dad-1 gag.

36. A transgenic plant, plant tissue or plant cell comprising a genome having a stably integrated nucleotide sequence of heterologous origin which comprises a coding sequence of a p35, iap or dad-1 gene.

37. The transgenic plant, plant tissue or plant cell of claim 36, wherein said nucleotide sequence comprises a coding sequence of a p35 gene.

38. The transgenic plant, plant tissue or plant cell of claim 36, wherein said nucleotide sequence comprises a coding sequence of an iap gene.

39. The transgenic plant, plant tissue or plant cell of claim 36, wherein said nucleotide sequence comprises a coding sequence of a dad-1 gene.

40. A transgenic maize plant, tissue or cell comprising a genome having a stably integrated nucleotide sequence of heterologous origin comprising a coding sequence of a p35 gene.

41. A transgenic maize plant, tissue or cell comprising a genome having a stably integrated nucleotide sequence of heterologous origin which comprises a coding sequence of an iap gene.

42. A transgenic maize plant, tissue or cell comprising a genome having a stably integrated nucleotide sequence of heterologous origin which comprises a coding sequence of a dad-1 gene.

43. The transgenic maize plant, tissue or cell of claim 40, 41 or 42 wherein said coding sequence comprises maize preferred codons.

44. A gramineceous plant cell or tissue culture medium, comprising
  (a) (i) an ethylene inhibitor other than silver nitrate, or (ii) an ethylene synthesis inhibitor; and
  (b) an Agrobacterium comprising a plasmid comprising a gene construct.

45. The transgenic plant, plant tissue or plant cell of claim 35 or 36, wherein said coding sequence comprises a synthetic nucleotide sequence comprising codons which are preferred by said transgenic plant, plant tissue or plant cell.

46. A fertile transgenic plant produced by the method according to claim 15.

47. The fertile transgenic plant of claim 46 which is a gramineceous plant.

48. The fertile transgenic plant of claim 46 which is a maize plant.

* * * * *

SEQUENCE LISTING

```
(1) GENERAL INFORMATION:

(iii) NUMBER OF SEQUENCES: 12

(2) INFORMATION FOR SEQ ID NO: 1:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
          (B) CLONE: PAT1

(xi) SEQUENCE DESCRIPTION: SEQ ID NO: 1:
```

```
TGTCTCCGGA GAGGAGACC                                                  19

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: PAT2

(xi) SEQUENCE DESCRIPTION: SEQ ID NO: 2:

CCAACATCAT GCCATCCACC                                                 20

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: MTL (P)

(xi) SEQUENCE DESCRIPTION: SEQ ID NO: 3:

AGGTGTCCAT GGTGCTCAAG                                                 20

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: iap (I)

(xi) SEQUENCE DESCRIPTION: SEQ ID NO: 4:

ACAATCGAAC CGCACACGTC                                                 20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)
```

(iii) HYPOTHETICAL: NO (iii) ANTI-SENSE: NO (vii) IMMEDIATE SOURCE:
              (B) CLONE: p35 (35)

(xi) SEQUENCE DESCRIPTION: SEQ ID NO: 5:

CCAGGTAGCA GTCGTTGTGT                                                          20

(2) INFORMATION FOR SEQ ID NO: 6:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
              (B) CLONE: dad-1 (D)

(xi) SEQUENCE DESCRIPTION: SEQ ID NO: 6:

CCTTGTTTCC TTTGTTCACT                                                          20

(2) INFORMATION FOR SEQ ID NO: 7:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 7:

GGTCCTATAC GAAGCGTTAC                                                          20

(2) INFORMATION FOR SEQ ID NO: 8:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 8:

CCACGTAGCA GTCGTTGTGT                                                          20

(2) INFORMATION FOR SEQ ID NO: 9:

(i) SEQUENCE CHARACTERISTICS:
              (A) LENGTH: 20 base pairs
              (B) TYPE: nucleic acid
              (C) STRANDEDNESS: single
              (D) TOPOLOGY: linear

```
        (ii) MOLECULE TYPE: DNA (genomic)

(iii) HYPOTHETICAL: NO (iii) ANTI-SENSE: NO (xi) SEQUENCE DESCRIPTION: SEQ ID NO: 9:

CATGTCTGAC TTGCGATTGG                                                        20

(2) INFORMATION FOR SEQ ID NO: 10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 10:

ACAATCGAAC CGCACACGTC                                                        20

(2) INFORMATION FOR SEQ ID NO: 11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 11:

GGAGAGGCGG TGTTAGTT                                                          18

(2) INFORMATION FOR SEQ ID NO: 12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 12:

CATCATCGCA TTCGAGAG                                                          18
```